United States Patent [19]

Grätzel et al.

[11] Patent Number: 4,847,231

[45] Date of Patent: Jul. 11, 1989

[54] MIXED RUTHENIUM CATALYST

[75] Inventors: Michael Grätzel, St-Sulpice; John Kiwi, Echandens; Krishnan R. Thampi, Chavannes, all of Switzerland

[73] Assignee: Gas Research Institute, Chicago, Ill.

[21] Appl. No.: 204,172

[22] Filed: Jun. 8, 1988

[51] Int. Cl.$^4$ .................. B01J 21/04; B01J 21/06; B01J 23/46; B01J 29/04

[52] U.S. Cl. .................. 502/74; 502/302; 502/303; 502/325; 502/326; 502/328; 502/329; 502/331; 502/332

[58] Field of Search ............... 502/74, 302, 303, 325, 502/326, 328, 329, 332, 331

[56] References Cited

U.S. PATENT DOCUMENTS

| | | | |
|---|---|---|---|
| 4,042,614 | 8/1977 | Vannice et al. | 260/449 R |
| 4,132,672 | 1/1979 | Wise et al. | 252/466 B |
| 4,477,595 | 10/1984 | Madon | 518/715 |
| 4,558,030 | 12/1985 | Arcuri et al. | 502/325 |
| 4,567,205 | 1/1986 | Arcuri et al. | 518/715 |
| 4,619,910 | 10/1986 | Dyer et al. | 502/336 |

OTHER PUBLICATIONS

K. W. Frese, Jr. and S. Leach "Electrochemical Reduction of Carbon Dioxide to Methane, Methanol, and CO on Ru Electrodes", Journal of the Electrochemical Society, vol. 132, No. 1, pp. 259–260.

Itamar Willner, R. Maidan, D. Mandler, Heinz Durr, G. Dorr and K. Zergerle, "Photosensitized Reduction of $CO_2$ to $CH_4$ and $H_2$ Evolution in the Presence of Ruthenium and Osmium Colloids; Strategies to Design Selectivity of Products Distribution", J. Am. Chem. Soc., vol. 109, No. 20, pp. 6080–6086, 1987.

Lunde, P. J. and Kester, F. L., J. Catal. 30, 423–429 (1973).

Phyng Quzck, T. Q. and Rouleau, D., J. Appl. Chem. Biotechnol. 26, 527–535 (1976).

Tomsett, A. D., Hagiwara, T., Miyamoto, A. and Inui, T., Appl. Catal., 26, 391–394 (1986).

Solymosi, F., Erdoheli, A. and Bansagi, T., J. Catal. 68, 372–381 (1981).

Weatherbee, G. D. and Bartholomew, C. H., J. Catal., 87, 352–362 (1984).

Inui, T., Funabiki, F., Suehiro, M. and Sezume, T., JCS Faraday Trans. 1, 75, 787–802 (1979).

*Primary Examiner*—W. J. Shine
*Attorney, Agent, or Firm*—Thomas W. Speckman

[57] ABSTRACT

A catalyst having a mixture of Ru and $RuO_x$, wherein x is greater than 0 and equal to or less than 2, supported by a suitable metal oxide support material is suitable for the heterogeneous catalytic gas phase direct methane production from hydrogen and carbon dioxide at mild temperatures as low as 25° C. and atmospheric pressure. Photo-methanation using such catalysts having photo-excitable support materials significantly increases the rate of methane production and the methane yield, yielding almost stoichiometrically quantitative amounts of methane according to the Sabatier reaction.

19 Claims, 1 Drawing Sheet

MIXED RUTHENIUM CATALYST

BACKGROUND OF THE INVENTION

1. Field of the Invention

Heterogeneous catalytic gas phase methane production from hydrogen and carbon dioxide is achieved directly at temperatures as low as 25° C. and at atmospheric pressures by use of a catalyst having a mixture of Ru and RuOx, wherein x is greater than 0 and equal to or less than 2, supported by a suitable metal oxide support. Photo-methanation using such catalysts having photo excitable support materials significantly increases methane production, yielding almost stoichiometrically quantitative amounts of methane according to Sabatier reaction.

2. Description of the Prior Art

Use of ruthenium as a hydrogenation catalyst on a titania support for Fischer-Tropsch reactions of CO and $H_2$ to produce hydrocarbons, principally liquid hydrocarbons at elevated pressure and methane at atmospheric pressure, is known from a number of patents including U.S. Pat. Nos. 4,042,614; 4,477,595; 4,558,030; 4,567,205; and 4,619,910. The 4,047,614 and 4,477,595 patents teach suppression of methane formation in the Fischer-Tropsch reaction when using titania as opposed to alumina or carbon support material.

Nickel is a known hydrogenation catalyst for reforming of methane by reaction of carbon monoxide and hydrogen. U.S. Pat. No. 4,132,672 teaches addition of a small amount of iridium for improved conversion of hydrogen and carbon monoxide to methane.

The electrochemical reduction of carbon dioxide to methane on Ru electrodes is taught by K. W. Frese, Jr. and S. Leach "Electrochemical Reduction of Carbon Dioxide to Methane, Methanol, and CO on Ru Electrodes", Journal of the Electrochemical Society, Vol. 132, No. 1, pgs. 259-260, January 1985. This electrochemical reduction works only at low current densities and is not a selective as desired for methane.

Photoreduction of $CO_2$ to methane and higher hydrocarbons in aqueous solution using Ru or Os colloids as catalysts is taught by Itamar Willner, Ruben Maidan, Daphna Mandler, Heinz Durr, Gisela Dorr and Klaus Zengerle, "Photosensitized Reduction of $CO_2$ to $CH_4$ and $H_2$ Evolution in the Presence of Ruthenium and Osmium Colloids: Strategies to Design Selectivity of Products Distribution", J. Am. Chem. Soc., Vol. 109, No. 20, pgs. 6080-6086, 1987. This photoreduction reaction utilizes Ru metal as an electron transfer catalyst and consumes triethanol amine making the process commercially unattractive.

The Sabatier reaction:

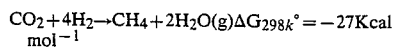
$$CO_2 + 4H_2 \rightarrow CH_4 + 2H_2O(g) \Delta G_{298k}° = -27 Kcal\ mol^{-1}$$

is a known important catalytic process which despite its favorable thermodynamics, has been difficult to achieve due to high energy intermediates imposing large kinetic barriers and the formation of side products is common. Investigations during recent years aimed toward improving the activity and selectivity of methanation catalysts has been reported, including Lunde, P. J. and Kester, F. L., J. Catal. 30, 423-429 (1973); Phyng Quack, T. Q. and Rouleau, D., J. appl. Chem. Biotechnol. 26, 527-535 (1976); Tomsett, A. D., Hagiwara, T., Miyamoto, A. and Inui, T., Appl. Catal., 26, 391-394 (1986); Solymosi, F., Erdoheli, A. and Bansagi, T., J. Catal. 68, 371-382 (1981); Weatherbee, G. D. and Bartholomew, C. H., J. Catal, 87, 352-362 (1984); and Inui, T., Funabiki, F., Suehiro, M. and Sezume, T., JCS Faraday Trans. 1, 75, 787-802 (1979). Although progress has been made, elevated temperatures of greater than 300° C. and pressures of greater than 1 atmosphere are still required for methane generation to proceed at significant rates and yields according to the Sabatier reaction.

SUMMARY OF THE INVENTION

It is an object of this invention to provide a low pressure and low temperature process for the direct formation of methane from carbon dioxide and hydrogen by a heterogeneous catalytic gas phase reaction.

It is another object of this invention to provide catalytic gas phase methane production from hydrogen and carbon dioxide using a mixed $Ru/RuO_x$ catalyst wherein x is greater than 0 and less than or equal to 2.

It is yet another object of this invention to provide a process for the direct formation of methane from carbon dioxide and hydrogen providing a very selective yield of methane of greater than about 95 percent, and preferably greater than 99 percent.

It is still another object of this invention to provide a process for catalytic direct methanation of carbon dioxide and hydrogen using highly dispersed mixture of $Ru/RuO_x$ on a photoexcitable catalyst support material wherein the reaction rate is significantly enhanced through photoexcitation of the support material.

The catalyst used in the process of this invention is a mixed ruthenium catalyst of about 10 to about 90 mole percent Ru and about 10 to about 90 weight percent $RuO_x$, wherein x is greater than 0 and less than and equal to 2. The mixed ruthenium catalyst is highly dispersed on a suitable metallic oxide support with Ru loading of about 1 to about 15 percent. Specifically, a mixed ruthenium catalyst of about 25 mole percent Ru and about 75 mole percent $RuO_x$ loaded onto a $TiO_2$ support material, Ru loading of 3.8 percent, has been found to provide very selective, greater than 99 percent, yield of methane by direct reaction of $CO_2$ and $H_2$ at about ambient temperature and atmospheric pressure. Reaction rates may be enhanced in the order of four to five times by photoexcitation of the $TiO_2$ support material under photoexcitation of the support material stoichiometry according to the Sabatier reaction continued to be greater than 99 percent at 1 atmosphere pressure and 46° C.

BRIEF DESCRIPTION OF THE DRAWING

Further features of the present invention will be apparent from the following more detailed description read in conjunction with the drawing, wherein.

DESCRIPTION OF PREFERRED EMBODIMENTS

Figure 1:
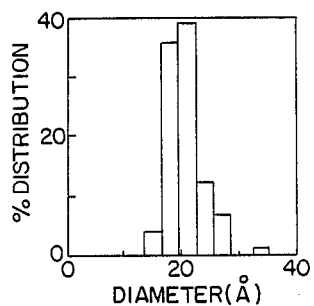
FIG. 1 is a bargraph showing size distribution of catalyst particles as prepared in Example I.

The process of this invention provides highly selective direct formation of methane from carbon dioxide and hydrogen according to the stoichiometry of the Sabatier reaction. High methane selectivity and yield is achieved at low temperatures and low pressures by use of a catalyst of a mixture of Ru and $RuO_x$ highly dispersed on specific metal oxide support materials.

The mixed ruthenium portion of the catalyst comprises about 10 to about 90 mole percent Ru and about 10 to about 90 mole percent $RuO_x$ wherein x is a number greater than 0 and less than and equal to 2. Preferred proportions of the mixed ruthenium catalyst are about 15 to about 35 mole percent Ru and about 65 to about 85 mole percent $RuO_x$. Catalytic activity of the mixed ruthenium catalyst has been found to be superior to use of the fully reduced Ru or the unreduced $RuO_2$ in the methanation reaction.

The support portion of the catalyst is a metal oxide which may be photoinsensitive for dark methanation or a semiconducting oxide for light activated methanation. The metal oxide support is selected from the group consisting of $TiO_2$, $ZrO_2$, $HfO_2$, $ThO_2$, $Nb_2O_5$, $La_2O_3$, $In_2O_3$, $SrTiO_3$, $CaTiO_3$, $BaTiO_3$, $LuCrO_4$, $Ac_2O_3$, ZnO, $Cu_2O$, NiO, $Bi_2O_3$, $Pb_3O_4$, $LuRhO_3$, $Al_2O_3$ and zeolites. The $Al_2O_3$ and zeolites are suitable for dark methanation. Preferred support materials include $TiO_2$, $ZrO_{26}$, $HfO_2$, $Nb_2O_5$, $La_2O_3$, and $ThO_2$, a particularly preferred support material is $TiO_2$. In the case of $TiO_2$, mixtures of anatase and rutile forms work very well as support material in this invention, pure anatase and pure rutile have also yielded good results when used in conjunction with the mixed ruthenium as a catalyst according to this invention. The support material in the catalyst of this invention is an active support as shown by Example II wherein $SiO_2$ and $Al_2O_3$ support materials have been found to not provide a satisfactory support material for photo-methanation catalysts according to this invention.

Loading of mixed Ru and $RuO_x$ on the support material in accordance with this invention should be about 1 to about 15 weight percent of the total mixed ruthenium/support material catalyst, preferably about 2.5 to about 7.5 weight percent. The powdered catalyst of this invention may be used in catalytically effective quantities and in any suitable manner known to the art for conduct of solid catalyst/gas phase reactions as known to the art. Hourly space velocities up to 100,000 $h^{-1}$ have been employed and gave good conversions.

Suitable catalysts maybe produced by the method set forth in Example I. During hydrolysis of the $RuCl_3$ catalyst precursor in the aqueous suspension containing the support material, the temperature is suitably about 30° to about 90° C., preferably about 60° to about 70° C. When carried out at 60° to 70° C., ruthenium clusters are formed with sizes of 10 to 20 Å; at 70° to 80° C., clusters of 35 to 65 Å are formed; and at 80° to 90° C., clusters in the order of 100 Å are formed. Hydrolysis may be carried out at a pH of about 2.5 to about 10, preferably about pH 4. The catalyst is reduced immediately prior to use in a stream of about 50 percent argon and 50 percent hydrogen for one hour at about 220° C. The reduction step controls the metallic character of the mixed $Ru/RuO_x$. $Ru/RuO_x$ particles supported on alumina or zeolites for dark methanation may be prepared in the same manner as for the semiconducting oxides catalysts. Alternatively, in the case of zeolite, an exchangeable cation of the zeolite may be exchanged with ruthenium(III)hexamine complex with subsequent calcination and reduction following the above described procedure. An alternative procedure for obtaining an active low temperature methanation catalyst is to impregnate titanium dioxide powder with ruthenium acetylacetonate solution in toluene as a solvent and calcining at about 400° C. Any process resulting in the above defined mixed ruthenium metal oxide catalyst is suitable.

The direct reduction of carbon dioxide to methane by hydrogen according to the Sabatier reaction is highly selectively achieved by the process of this invention under low pressure and low temperature conditions. The process of this invention is carried out by passing gaseous carbon dioxide and hydrogen in contact with the mixed ruthenium/metallic oxide support catalyst of this invention. It is preferred that hydrogen be present in stoichiometric excess amounts, about 1 to about 5 times the stoichiometric amount required for the Sabatier reaction being suitable, about 2 to about 4 times stoichiometric hydrogen being preferred. The process for direct formation of methane from carbon dioxide and hydrogen according to this invention is carried out at low pressure, ambient up to about 10 atm, preferably ambient to about 3 atm. The process is suitably carried out at low temperatures below about 300° C. and preferably below 200° C., ambient to about 200° C. being suitable, about 50° to about 150° being preferred.

The process of this invention appears to proceed directly according to the Sabatier reaction. Analyses of gas mixtures during the process have found no evidence of formation of carbon monoxide and Fischer-Tropsch products, as further set forth specifically in Example II. This has been further confirmed by separate work showing that the hydrogenation of carbon monoxide using the catalyst of this invention requires much higher temperatures than the mild near ambient conditions suitable for the process of this invention. Still further, the direct conversion of carbon dioxide to methane according to the present process has been found to be very selective, the yield of methane being greater than 99 percent under many conditions. To the inventors' knowledge, the catalyst of this invention provides the first process for ambient room temperature conversion of carbon dioxide to methane.

Figure 3:
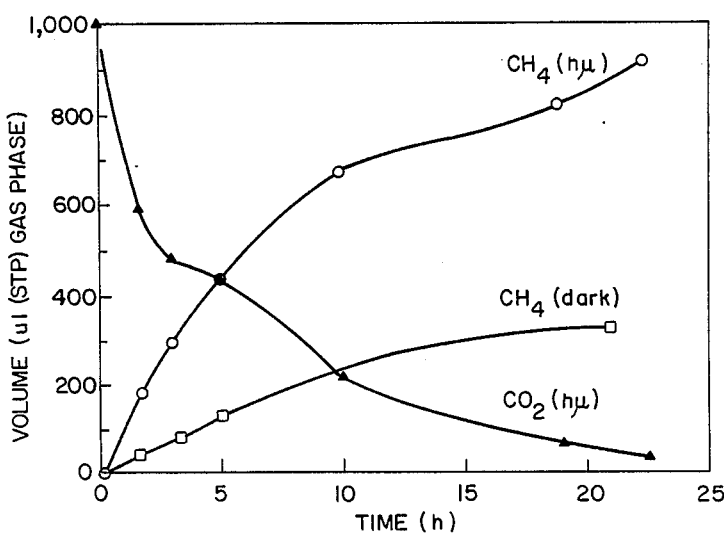
FIG. 3 is a plot showing production of methane as a function of time in the dark phase as described in Example II and under photo-methanation conditions as described in Example III.

The rate of the Sabatier reaction according to the process of this invention, may be significantly increased by photoexcitation of the support material. As shown in FIG. 3, photo-methanation as described in Example II occurred at initial rates of 4 to 5 times that of dark methanation as shown in FIG. 3 and described in Example II. Even more important with respect to photo-methanation, significantly higher quantities of carbon dioxide were reacted thereby avoiding the leveling off at about 30 percent carbon dioxide reaction noted for dark methanation and shown in FIG. 3.

To aid in the elucidation of the mechanism of photo-methanation, investigation was conducted on the portion of the light spectrum active in enhancing the rate of methanation. In this work, carried out at 25° C. using a 150 watt high pressure Xe lamp equipped with a water jacket to remove infrared radiation, a 695 nm cutoff filter was placed in the light beam and methanation proceeded at essentially the same rate as in the dark, at 0.17 $\mu$mol $h^{-1}$. Changing to a 435 nm cutoff filter increased the rate only slightly to 0.27 $\mu$mol $h^{-1}$. When the filters were removed and no filter was used admitting bandgap radiation to the sample, 0.54 $\mu$mol $h^{-1}$ rate of photo-methanation was achieved. When no filter was used, the short ultraviolet radiation ($\lambda < 310$ nm) is removed by the Pyrex wall of the reactor. Since the fraction of light emitted by the lamp in the 310 nm to 435 nm region is less than 5 percent of the total intensity, it is seen that bandgap excitation of the $TiO_2$ support is the dominant contribution to the photo enhancement of the methanation reaction.

Although the mechanism is not thoroughly understood, redox processes involving electron-hole pairs are likely to be important in the photo-reaction. These may lead to the generation of high-energy intermediates which are difficult to form in the dark at room temperature. An important role in the methanation of $CO_2$ on Ru is played by carbidic surface carbon (Ru-C). The enthalpy of Ru-C formation is 100 kJ mol$^{-1}$ positive with respect to graphite and does not depend upon surface coverage, indicating the existence of isolated carbon atoms coordinated to Ru without the formation of graphitic islands for overlays. Photogeneration of such Ru-C species would involve bandgap excitation of the $TiO_2$ resulting in electron-hole pair formation:

$$TiO_2 \xrightarrow{h\nu} TiO_2(e_{cb}^-, h_{vb}^+) \quad (1)$$

followed by reduction of $CO_2$ $$4e^- + CO_2 \xrightarrow{Ru} Ru-C + 2O^{2-} \quad (2)$$

The concomitant valence band process could involve hydrogen oxidation $$2H_2 + 4h^+_{vb} \rightarrow 4H^+ \quad (3)$$

followed by neutralization $$4H^+ + 2O^{2-} \rightarrow 2H_2O \quad (4)$$

Methane is subsequently generated in the reaction of surface carbon with hydrogen:

$$Ru-C + 2H_2 \rightarrow Ru + CH_4 \quad (5)$$

The thermal methanation could proceed by a similar mechanism. But the generation of carbidic surface carbon would involve the thermal reduction of adsorbed $CO_2$ by coadsorbed hydrogen:

$$(CO_2)_{ad} + 2(H_2)_{ad} \xrightarrow{Ru} RuC + 2H_2O \quad (6)$$

The mechanism postulated here is plausible in view of the fact that reactions (2) and (5) have been found to occur in the cathodic reduction of $CO_2$ to methane on Ru electrodes and colloids. However, photoelectronic effects such as the increase in the electrical conductivity of the support under light excitation could also be important.

The following examples set forth specific embodiments in detail and are meant to exemplify the invention and not to limit it in any way.

EXAMPLE I

Highly dispersed Ru/RuO$_x$ (x less than or equal to 2) was loaded onto $TiO_2$ as a catalyst by dissolving 100 mg RuCl$_3$·3H$_2$O (alpha inorganic; Ru content 38 percent) in 100ml 0.1 M HCl and the solution left to equilibrate for one day. One gram $TiO_2$ (P25 powder, a mixture of 80 percent anatase and 20 percent rutile; BET surface area 55 m$^2$g$^{-1}$; density 3.8 g cm$^{-3}$; obtained from Degussa, West Germany) was added and the pH increased to 4.5 by adding 0.1 M KOH solution. The temperature of the dispersion was raised to 60° C. and maintained for a period of five hours during which the pH was repeatedly readjusted to 4.5. Water was subsequently evaporated by heating the dispersion in an open dish until it boiled and the solid was calcined for 20 hours at 170° C. followed by 12 to 18 hours at 375° C. Residual KCl was removed from the catalyst by dialysis which was carried out over a period of two days. Subsequently, the catalyst was dried overnight at 110° C. This procedure yielded RuO$_2$ particles of 10-20 Å size. The RuO$_2$ was partially reduced in a H$_2$/Ar (1:1) stream (flow rate 40 ml h$^{-1}$) at 220° C. for one hour yielding a catalyst having 75 percent RuO$_x$ (x less than or equal to 2) and 25 percent Ru, as shown by X-ray photoelectron spectroscopy analysis. The dispersion of Ru determined by conventional H$_2$ adsorption measurement was 50-55 percent, assuming a 1:1 stoichiometry for the chemisorption of hydrogen atoms by surface Ru. This high dispersion value excludes strong metal-support interactions which suppress H$_2$ adsorption. This is expected from the relatively low temperature employed in the reduction which renders the formation of such a state very unlikely. Transition electron microscopy showed catalyst particles with an average diameter of 20 Å and size distribution shown in FIG. 1. Assuming the particles have a spherical shape the calculated dispersion is 65 percent. Ru loading of 3.8 percent was confirmed by elemental analysis.

Figure 2:
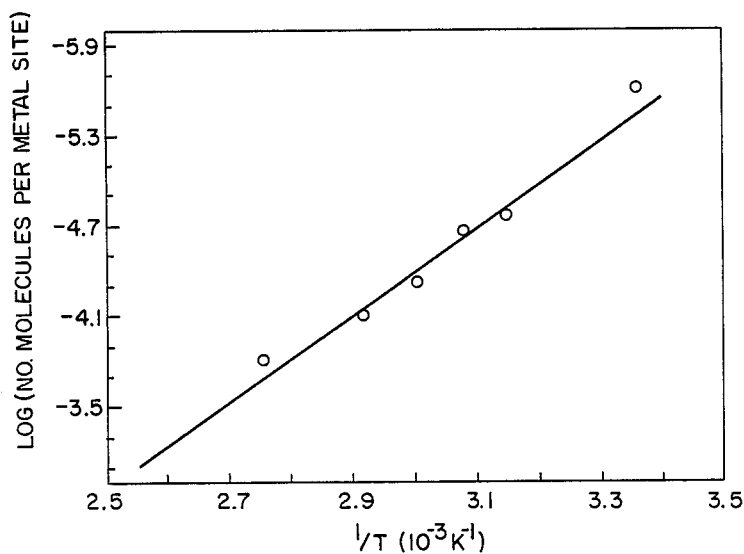
FIG. 2 is a plot of turnover frequencies measured at various temperatures in accordance with Example II.

EXAMPLE II 100 mg catalyst powder as prepared in Example I was spread over the bottom of a flat Pyrex reactor vessel (volume 20 cm$^3$) equipped with a side arm and a septum for the admission and withdrawal of gas samples. Exposure of the catalyst to air after reduction was avoided by maintaining it under argon and the transfer to the reactor was performed in a glove box with reaction temperature controlled by a microprocessor. Methane formation was conducted in the dark. The reactor initially contained 1 ml $CO_2$(P$_{CO2}$=0.05 atm) and 12 ml H$_2$(P$_{H2}$=0.6 atm). The remaining gas was argon with traces of nitrogen, the total pressure was 1 atm. Several runs were made under the same conditions except the temperature was varied from 25° to 90° C. Methane was formed in the presence of the $TiO_2$/Ru/RuO$_x$ catalyst at a temperature of 25° C. When methanation was complete, any water soluble product was extracted from the reaction system with 1 ml of water. After the catalyst was centrifuged, the supernatant was analyzed by high pressure liquid chromatography. Blank experiments showed the detection limit to be a factor of 500 below the quantity of methane produced. Thus, the overall selectivity of the catalyst was greater than 99 percent. Initial rates of methane formation were 0.17 μmol h$^{-1}$ at 25° C. and 10.5 μmol h$^{-1}$ at 90° C. These rates correspond to turnover frequencies of 2.5×10$^{-6}$ s$^{-1}$ and 1.6×10$^{-4}$ s$^{-1}$, respectively, based upon 50 percent Ru dispersion. From the slope of an Arrhenius plot of the turnover frequencies measured in the temperature range from 25° to 90° C. shown in FIG. 2, the slope of the straight line showed an activation energy of 54 kJ mol$^{-1}$. Published activation values for methanation of carbon dioxide range from 30 to 171 kJ mol$^{-1}$, depending upon catalyst and support material at elevated temperatures of greater than 400° K.

Production of methane in the dark at 46° C. as a function of time is shown in FIG. 3 by the curve marked "CH$_4$(dark)".

Methane formation and carbon dioxide consumption strictly obeyed the 1:1 stoichiometry of the Sabatier reaction indicating that the catalyst operated in a very selective fashion. This was confirmed by gas chromotograph, mass spectrometry and high pressure liquid chromotography which failed to detect other byproducts. Particularly, the formation of carbon monoxide, methanol, formaldehyde, ethane and higher homologues can be excluded within the detection limit for these compounds which was at least 0.002 $\mu$mol per $\mu$mol of methane generated. There was no formation of formic acid or oxalic acid.

SiO$_2$/Ru/RuO$_x$ and Al$_2$O$_3$/Ru/RuO$_x$ were prepared in the same manner as TiO$_2$/Ru/RuO$_x$ and tested for methanation under identical conditions and found to be inactive as photo-methanation catalysts at 25° C.

EXAMPLE III

Photo-methanation was conducted under the same conditions as set forth in Example II except that the TiO$_2$/Ru/RuO$_x$ catalyst was subjected to bandgap illumination. TiO$_2$ is a semiconductor (bandgap 3 eV) which absorbs near-ultraviolet radiation. Illumination was achieved with a solar simulator as the light source providing a total intensity of 0.08 W cm$^{-2}$. The temperature of the catalyst was maintained at 46° C. Methane was produced at an initial rate of 116 $\mu$l h$^{-1}$ (STP). FIG. 3 shows the increase in methane and decrease in CO$_2$ as a function of illumination time. It is seen that within five hours of photolysis, 450 $\mu$l of CH$_4$ had been produced and the same amount of CO$_2$ remained in the gas phase. As FIG. 3 shows, during photo-methanation, the number of moles of methane and CO$_2$ present in the gas phase add up to less than the number of moles of CO$_2$ initially injected which is due to co-adsorption of CO$_2$ and hydrogen on the catalyst surface. This was verified by measuring the adsorption isotherms of CO$_2$ in the absence and presence of hydrogen. Photo-conversion of CO$_2$ to methane was almost complete after 22 hours, as compared to dark methanation which occurred at rates 4 to 5 times less than the initial rate of photo-methanation, the dark methanation leveling off after about 22 hours when about 30 percent of the CO$_2$ had reacted. The decrease in the rate was attributed to accumulation of liquid water which appears to retard the reaction.

After a first photo-methanation run of 22 hours, the gas mixture was flushed from the reactor and H$_2$O removed in an argon stream maintained at 100° C. after which injection of 1 ml CO$_2$ and 12 ml H$_2$ was repeated and illumination by the solar simulator repeated with the same catalyst. This procedure was repeated ten times producing a total volume of 11 ml of CH$_4$ corresponding to a turnover number of 28 with respect to the surface Ru atoms, without decline in catalytic activity.

Analysis of the reaction products was made, as described in Example II, and there was not evidence of the formation of compounds other than methane, showing stoichiometry of the Sabatier reaction (greater than 99 percent). At $P_{CO_2}=1$ atm and temperature 46° C., the extrapolated turnover frequency was $1.4 \times 10^{-3}$ s$^{-1}$.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A mixed ruthenium catalyst comprising a mixture of about 10 to about 90 mole percent Ru and about 10 to about 90 mole percent RuO$_x$, wherein x is a number greater than 0 and equal to or less than 2, highly dispersed on a support selected from the group consisting of semiconducting oxides selected from the group consisting of TiO$_2$6, ZrO$_2$, HfO$_2$, ThO$_2$, Nb$_2$O$_5$, La$_2$O$_3$, In$_2$O$_3$6, SrTiO$_3$, BaTiO$_3$, CaTiO$_3$, LuCrO$_4$, Ac$_2$O$_3$, ZnO, Cu$_2$O, NiO, Bi$_2$O$_3$, Pb$_3$O$_4$, and Al$_2$O$_3$, and zeolites.

2. A catalyst according to claim 1, wherein said support is a semiconducting oxide selected from the group consisting of TiO$_2$, ZrO$_2$, HfO$_2$, ThO$_2$, Nb$_2$O$_5$, La$_2$O$_3$6, In$_2$O$_3$, SrTiO$_3$, BaTiO$_3$, CaTiO$_3$, LuCrO$_4$, Ac$_2$O$_3$, ZnO, Cu$_2$O, NiO, Bi$_2$O$_3$, Pb$_3$O$_4$, and LuRhO$_3$.

3. A catalyst according to claim 2 wherein said semiconducting oxide is TiO$_2$.

4. A catalyst according to claim 1 wherein said mixture is about 15 to about 35 mole percent Ru and about 65 to about 85 mole percent RuO$_x$.

5. A catalyst according to claim 1 wherein loading of said mixture on said support is about 1 to about 15 weight percent of the total mixed ruthenium/support material catalyst.

6. A catalyst according to claim 1 wherein loading of said mixture on said support is about 2.5 to about 7.5 weight percent of the total mixed ruthenium/support material catalyst.

7. A catalyst according to claim 1 wherein said support is selected from the group consisting of Al$_2$O$_3$ and zeolites.

8. A catalyst according to claim 2 wherein said semiconducting oxide is selected from the group consisting of TiO$_2$, ZrO$_2$, HfO$_2$, Nb$_2$O$_5$, La$_2$O$_3$, and ThO$_2$.

9. A catalyst according to claim 8 wherein said mixture is about 15 to about 35 mole percent Ru and about 65 to about 85 mole percent RuO$_x$.

10. A catalyst according to claim 8 wherein loading of said mixture on said support is about 1 to about 15 weight percent of the total mixed ruthenium/support material catalyst.

11. A catalyst according to claim 8 wherein loading of said mixture on said support is about 2.5 to about 7.5 weight percent of the total mixed ruthenium/support material catalyst.

12. A catalyst according to claim 3 wherein said mixture is about 15 to about 35 mole percent Ru and about 65 to about 85 mole percent RuO$_x$.

13. A catalyst according to claim 3 wherein loading of said mixture on said support is about 1 to about 15 weight percent of the total mixed ruthenium/support material catalyst.

14. A catalyst according to claim 3 wherein loading of said mixture on said support is about 2.5 to about 7.5 weight percent of the total mixed ruthenium/support material catalyst.

15. A catalyst according to claim 3 wherein said TiO$_2$ is a mixture of anatase and rutile forms.

16. A catalyst according to claim 3 wherein said TiO$_2$ is in anatase form.

17. A catalyst according to claim 3 wherein said TiO$_2$ is in rutile form.

18. A catalyst according to claim 1 wherein said support is Al$_2$O$_3$.

19. A catalyst according to claim 1 wherein said support is a zeolite.

* * * * *